United States Patent [19]
Kerin et al.

[11] Patent Number: 5,935,056
[45] Date of Patent: Aug. 10, 1999

[54] ACCESS CATHETER AND METHOD FOR MAINTAINING SEPARATION BETWEEN A FALLOPOSCOPE AND A TUBAL WALL

[75] Inventors: John Kerin, North Adelaide, Australia; Charles Milo, Union City, Calif.; Julian Nikolchev, Portola Valley, Calif.; James Doty, Larkspur, Calif.

[73] Assignee: Conceptus, Inc., San Carlos, Calif.

[21] Appl. No.: 08/925,594

[22] Filed: Sep. 8, 1997

Related U.S. Application Data

[62] Division of application No. 08/544,384, Oct. 10, 1995, Pat. No. 5,716,321.

[51] Int. Cl.⁶ ........................................................... A61B 1/01
[52] U.S. Cl. ........................... 600/114; 600/127; 600/135; 604/280
[58] Field of Search ..................................... 600/104, 127, 600/114–116, 129, 585; 604/280, 264, 95, 96

[56] References Cited

U.S. PATENT DOCUMENTS

| | | |
|---|---|---|
| 1,139,015 | 5/1915 | Cerbo ........................................ 600/129 |
| 1,621,159 | 3/1927 | Evans . |
| 3,866,601 | 2/1975 | Russell . |
| 4,198,960 | 4/1980 | Utsugi . |
| 4,306,566 | 12/1981 | Sinko . |
| 4,350,147 | 9/1982 | Sarrine . |
| 4,608,965 | 9/1986 | Anspach, Jr. et al. . |
| 4,717,387 | 1/1988 | Inoue et al. . |
| 4,779,611 | 10/1988 | Grooters et al. . |
| 4,793,326 | 12/1988 | Shishido . |
| 4,825,259 | 4/1989 | Berry, Jr. . |
| 4,846,812 | 7/1989 | Walker et al. . |
| 4,878,893 | 11/1989 | Chin . |
| 5,047,848 | 9/1991 | Krauter . |
| 5,099,827 | 3/1992 | Melzer et al. . |
| 5,263,928 | 11/1993 | Trauthen et al. . |
| 5,279,596 | 1/1994 | Castaneda et al. . |
| 5,306,261 | 4/1994 | Alliger et al. . |
| 5,307,814 | 5/1994 | Kressel et al. . |
| 5,308,342 | 5/1994 | Sepetka et al. . |
| 5,358,496 | 10/1994 | Oritz et al. . |
| 5,385,152 | 1/1995 | Abele et al. . |
| 5,445,142 | 8/1995 | Hassler, Jr. .............................. 600/114 |
| 5,448,990 | 9/1995 | De Faria-Correa ..................... 600/129 |
| 5,505,686 | 4/1996 | Willis et al. . |
| 5,509,900 | 4/1996 | Kirkman ................................. 604/280 |
| 5,536,234 | 7/1996 | Newman ................................. 600/104 |
| 5,667,475 | 9/1997 | Laser et al. ............................. 600/127 |
| 5,681,262 | 10/1997 | Isse ......................................... 600/127 |
| 5,700,236 | 12/1997 | Sauer et al. ............................ 600/129 |
| 5,746,692 | 5/1998 | Bauch et al. ........................... 600/104 |

OTHER PUBLICATIONS

Kerin et al., "Falloposcopy: A Microendoscopic Technique for Visual Exploration of the Human Fallopian Tube form the Uterotubal Ostium to the Fimria Using a Transvaginal Approach," *Fertility and Sterility*, vol. 54, No. 3, pp. 390–400 (1990).

Kerin et al., "Development and Application of a Falloposcope for Transvaginal Endoscopy of the Fallopian Tube," *J. aparoendoscopic Surgery*, vol. 1, pp. 47–56.

*Primary Examiner*—John P. Leubecker
*Attorney, Agent, or Firm*—Townsend and Townsend and Crew LLP

[57] ABSTRACT

A method and apparatus are provided for imaging a narrow body lumen, the method comprising maintaining separation between a distal end of an optical viewing scope and a lumen wall with a spacing structure which extends distally from the distal end of an access catheter. Optional spacing structures include distal cages and a guidewire which is fixed to and extends distally from the access catheter body. The invention is particularly beneficial during retrograde imaging of the fallopian tube, as it prevents the tubal wall from coming into such close proximity to a falloposcope as to produce "white-out" on the imaging monitor.

9 Claims, 7 Drawing Sheets

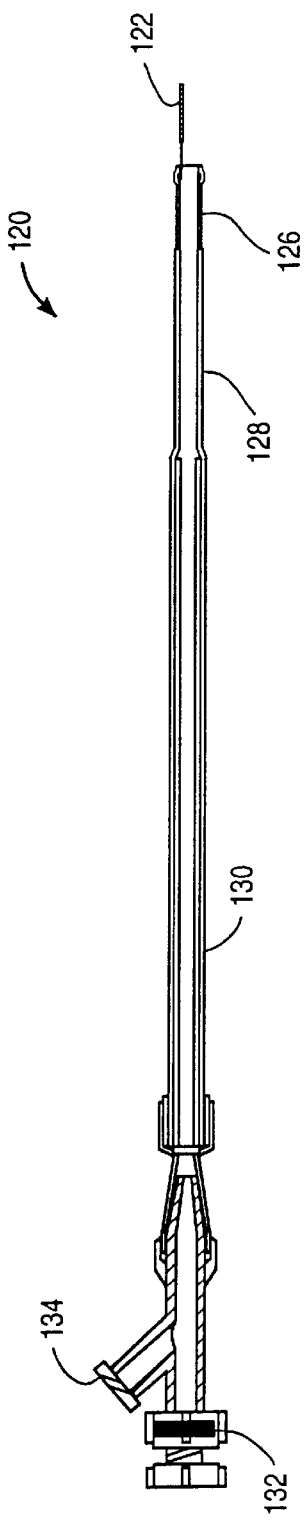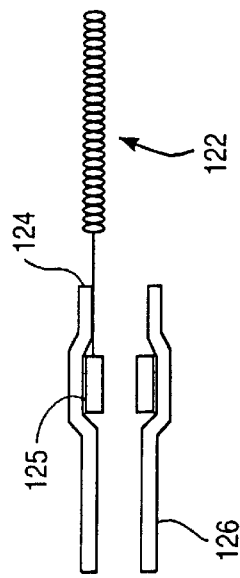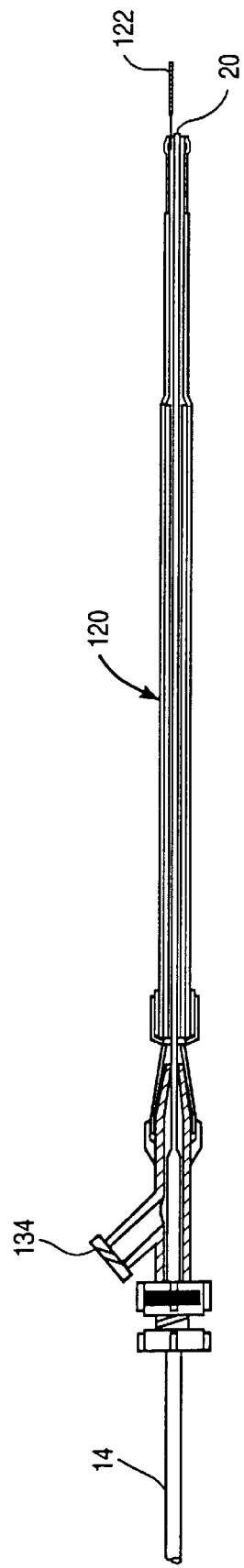

ACCESS CATHETER AND METHOD FOR MAINTAINING SEPARATION BETWEEN A FALLOPOSCOPE AND A TUBAL WALL

This is a Division of U.S. patent application Ser. No. 08/544,384, filed Oct. 10, 1995, now U.S. Pat. No. 5,716,321 the disclosure of which is incorporated by reference.

BACKGROUND OF THE INVENTION

1. Field of the Invention

The present invention relates generally to endoscopic surgical methods and apparatus. More particularly, the present invention provides an access catheter having a distally protruding structure which maintains separation between a viewing scope and a lumenal wall.

Diseases of the fallopian tubes are a major cause of infertility and tubal pregnancy. Until recently, diagnosis and treatment of tubal disease has been hampered by the difficulty in accessing and imaging the interior of the fallopian tube. Such difficulties, however, have been largely overcome by the recent availability of very small guidewires, catheters, and fiberoptic viewing scopes, usually referred to as falloposcopes. Using these instruments and systems, a physician can gain atraumatic access to the interior of the fallopian tube through a hysteroscope positioned within the uterus. Such falloposcopic imaging techniques were described by Kerin et al. in *Fertil. Steril.*, Vol. 54, pp. 390–400 (1990), and in *J. Laparoendoscopic Surg.*, Vol. 1, pp. 47–56.

Falloposcopic access and imaging techniques are generally performed as follows. A hysteroscope is positioned within the uterus and an irrigating solution is introduced to distend the uterus and permit video monitoring. A very small guidewire is then introduced through the hysteroscope and advanced past the ostium and into the fallopian tube. The guidewire will continue to be advanced until it approaches the distal fimbria. A small tubular access catheter may then be advanced through the hysteroscope and over the guidewire into the fallopian tube, again preferably approaching the distal fimbria. After removing the guidewire, the falloposcope (which is a small diameter fiberoptic bundling including both imaging and illumination fibers in a single shaft) is advanced until its distal end reaches the distal end of the access catheter. Imaging may then be performed in a retrograde manner with the falloposcope and access catheter being drawn outwardly together through the fallopian tube while producing an image on the associated video monitor. The lumen of the tubular access catheter will also provide an access path for devices, such as drug delivery catheters, small instruments, and the like, for treatment of tubal lumen disease.

While such retrograde falloposcopic imaging techniques represent a significant improvement, they still suffer from certain limitations. In particular, falloposcopes having both illumination and imaging fiberoptics require a minimum separation between the imaging lens at the end of the fiberoptic bundles and the tissue to be imaged. Unfortunately, the narrowly confined lumen of the fallopian tube contracts soon after the access catheter has been withdrawn. Hence, the tubal wall often collapses in on the withdrawing falloposcope during retrograde imaging, intruding upon the required imaging separation. As the tubal wall tissues come in close proximity with the imaging and illumination fiberoptics, excessive illumination light is reflected back to the imaging system, causing a partial or total "white-out" of the viewing monitor. These white-outs are a common and undesirable limitation on the effectiveness of retrograde imaging of the fallopian tube and other narrow body lumens.

It would therefore be desirable to provide improved methods and systems for imaging fallopian tubes and other narrow body lumens. It would be particularly desirable to provide improved access catheters and methods for their use which would reduce the incidence of white-out associated with the fallopian tubal wall approaching too close to the optical viewing scope. It would further be desirable if such improved methods and devices were compatible with and able to enhance the effectiveness of retrograde tubal imaging systems and methods.

2. Description of the Background Art

Kerin et al., *Fertil. Steril.*, Vol. 54, pp. 390–400 (1990), and in *J. Laparoendoscopic Surg.*, Vol. 1, pp. 47–56, have been described above. U.S. Pat. No. 4,793,326 describes an industrial endoscope having an elongated arm member to facilitate advancing separate illumination and observation windows past the abrupt steps of piping elbow joints. U.S. Pat. No. 4,717,387 describes an intercardiac catheter having a distal balloon for positioning the catheter with respect to a body surface to be viewed through an optical scope. U.S. Pat. No. 5,263,982 describes an endoscopic catheter having a laterally offset movable guidewire.

U.S. Pat. Nos. 5,047,848 and 4,825,259 disclose borescope having specialized distal tip gauges which permit optical measurements of imaged features. U.S. Pat. No. 4,608,965 discloses an endoscopic sheath having a Malecott-type structure for anchoring the scope in a body cavity.

U.S. Pat. No. 5,358,496 is representative of numerous instruments intended to be inserted through endoscopes. U.S. Pat. Nos. 3,866,601; 4,306,566; 4,350,147; 4,846,812; 5,099,827; 5,263,928; 5,279,596; 5,306,261; 5,307,814; 5,308,342; 5,385,152; are also relevant.

An exemplary falloposcopic imaging system is described in copending application Ser. No. 08/027,475, the full disclosure of which is incorporated herein by reference.

SUMMARY OF THE INVENTION

In a first aspect, the present invention provides a method for viewing a lumenal wall of. a narrow body lumen. The method of the present invention comprises introducing a catheter within a body lumen and positioning an optical viewing scope within a lumen of the catheter so that a distal end of the scope is at a scope viewing position adjacent to a distal end of the catheter. A spacing structure affixed to the distal end of the catheter maintains separation between the lumen wall and the scope. This separation helps prevent imaging white-out conditions which would otherwise occur when the optical viewing scope and body lumen wall are in close proximity. The lumenal wall is imaged through the scope while the distal end of the scope is in the scope viewing position proximate the spacing structure. Although the spacing structure will typically appear in the viewing monitor, blocking some portion of the lumen wall from imaging, the image quality and availability are nonetheless substantially enhanced. Preferably, the catheter is advanced distally of a target region of the body lumen during the introducing step, and the catheter and scope are proximally withdrawn while imaging through the distally oriented scope. This is generally referred to as "retrograde imaging."

In some embodiments, the imaging step comprises viewing the lumen wall at least in part through a cage disposed over the distal end of the scope. Alternatively, the spacing structure may comprise a guidewire which extends distally from the catheter, which guidewire may also be rotated during introduction of the catheter to maneuver the catheter through a body lumen system. Alternatively, the spacing structure may comprise a wire loop extending distally from the catheter body. Such a wire loop may be expanded by advancing a proximal length of the wire relative to the proximal end of the catheter. In this way, the size of the loop can be adjusted maintain separation between the body lumen wall and the optical viewing position.

In another aspect, the present invention provides an improved method for viewing a target region of a fallopian tube. The method is of the type including transcervically accessing the fallopian tube with the catheter and inserting an optical viewing scope within a lumen of the catheter so that distal ends of the scope and catheter are adjacent to each other, and then retrograde imaging the fallopian tube by withdrawing the scope and catheter together. The improvement comprises promoting axial alignment between the tubal wall and the distal end of the scope with a structure extending distally from the distal end of the catheter. Axial alignment between the distal end of the scope and the tubal wall will optionally comprise axially rotating the catheter to engage the structure against the tubal wall, where the structure is unsymmetrical about an axis of the catheter lumen. Advantageously, such an unsymmetrical spacing structure can be used to selectively engage only that portion of the tubal wall which is necessary to avoid a white-out. The unsymmetrical spacing structure further avoids blocking of the imaging view where not required to prevent intrusion of the tubal wall toward the viewing scope.

In another aspect, a catheter for viewing a wall of a narrow body lumen according to the principles of the present invention comprises an elongate tubular body having a proximal end, a distal end and a central lumen therebetween. The lumen receives a shaft of an optical viewing scope of the type including both illumination fibers and viewing fibers. The scope is received at a scope viewing position adjacent to the distal end of the body. Additionally, a spacing structure extends distally from the distal end, usually being fixed or coupled thereto, so as to separate the scope viewing position from the lumen wall. Advantageously, the catheter of the present invention need only include a single axial lumen, thereby minimizing its cross-sectional size. Preferably, the spacing structure is affixed with a coupler ring which fittingly engages the body, the coupler ring ideally being disposed within the body lumen and having an outer diameter which is larger than a relaxed lumen diameter. In some embodiments, the spacing structure comprises a cage disposed over the scope viewing position. The cage itself may comprise a distal extension of the body having a plurality of viewing slots, or may alternatively comprise a separate structure attached to the distal end of the catheter.

In some embodiments of the catheter of the present invention, the spacing structure comprises a guidewire which extends distally of the body, typically being cantilevered from the distal end of the catheter at the edge of a distal lumen opening. Ideally, the guidewire comprises a coiled distal section and an uncoiled section between the catheter and coil. This provides an increasing distal flexibility comparable to that of distally tapering guidewires, but with a decrease in proximal guidewire cross-section. The flexibility of the guidewire is ideally similar to tapered guidewires sold under the tradenames "Traveler" and "Robust" by Conceptus, Inc. of San Carlos, Calif., the present assignee. The guidewire may thus find use in maneuvering the catheter through the body lumen, and may also allow the catheter to be advanced while "antigrade" imaging through a scope at the scope viewing position. Such antigrade imaging will potentially provide a means for directing the catheter distally, and also provide a simultaneous image of the tubal wall. Alternatively, the spacing structure may comprise an expandable distal loop actuable by advancing a proximal portion or extension of the loop relative to the proximal end of the body. This provides a controllable separation between the lumen wall and the scope viewing position to overcome white-out conditions as they are encountered along the body lumen. As a further alternative, the spacing structure comprises one or more diagonal tips extending from the distal end of the body.

BRIEF DESCRIPTION OF THE DRAWINGS

FIGS. 10A, B and C illustrate a preferred access catheter having a distal guidewire for maintaining axial alignment and separation between a falloposcope and a surrounding fallopian tube.

DETAILED DESCRIPTION OF THE SPECIFIC EMBODIMENTS

Figure 1:
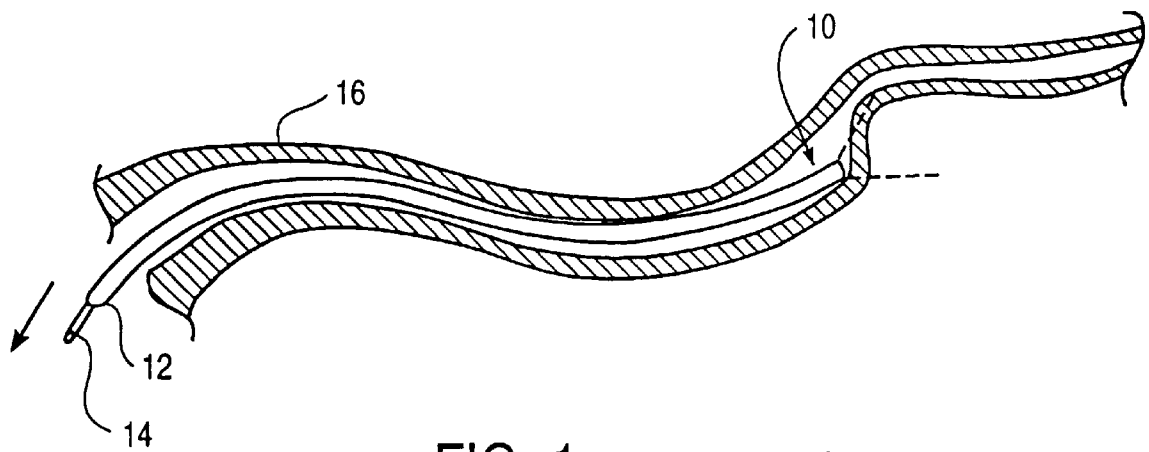
FIG. 1 illustrates a prior art access catheter and optical viewing scope used for retrograde imaging of a fallopian tube.
Figure 2:
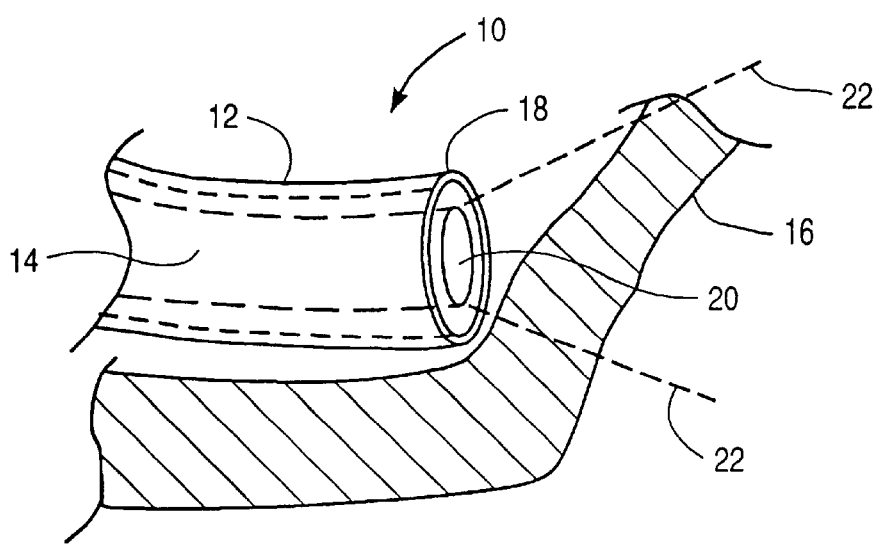
FIG. 2 is a detail view showing the distal ends of the access catheter and optical viewing scope of FIG. 1 in close proximity to the tubal wall, which is typical of the white-out conditions encountered when using the access catheters of the prior art.

Referring to FIGS. 1 and 2, a prior art retrograde fallopian tube viewing system 10 includes an access catheter 12 and a falloposcope 14. Prior art viewing system 10 is inserted to the distal portion of a fallopian tube 16, and is withdrawn proximally as indicated to provide retrograde imaging. Fallopian tube 16 is quite narrow and tortuous, and the tubal wall is highly flexible. Hence, as prior art imaging system 10 is withdrawn proximally, the tubal wall is distended by the access cover 12, and then collapses down to its relaxed shape after a distal end 18 of the access catheter has passed. As optimal imaging occurs when the distal end of the falloposcope is substantially aligned with the distal end of the access catheter, the tubal wall often comes into close proximity with distal end of falloposcope 20.

Falloposcope 14 generally includes two distinct types of optical fibers. The first group of optical fibers is used to transmit light to the distal end of falloposcope 20 to provide illumination for optical viewing. The second type of optical fiber, often comprising a single optical fiber bundle called a "coherent image fiber optic bundle," transmits an optical image from a lens at a distal end of falloposcope 20 to a proximal imaging apparatus. The image itself comprises the illumination light from the illumination fibers which is reflected by objects located within a field of view 22 of distal end of falloposcope 20. As the tubal wall comes into close proximity with both the illumination and optical viewing fibers at the distal end of the falloposcope, the imaging apparatus is unable to produce a coherent picture, and a partial or a total white-out occurs on the viewing monitor.

Figure 3:
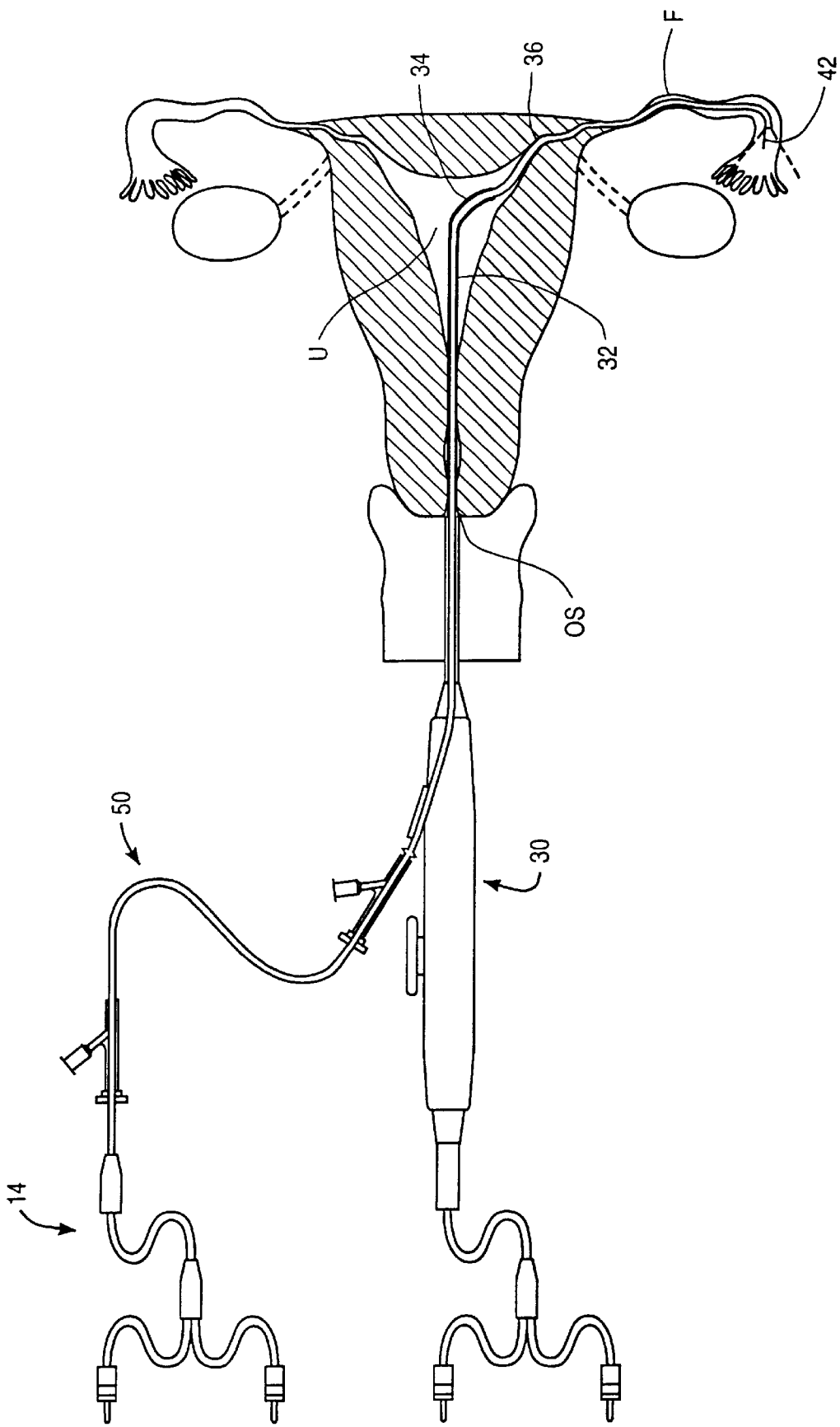
FIG. 3 illustrates a preferred combination of a hysteroscope, access catheter, and falloposcope for use in imaging a fallopian tube, according to the principles of the present invention.
Figure 4:
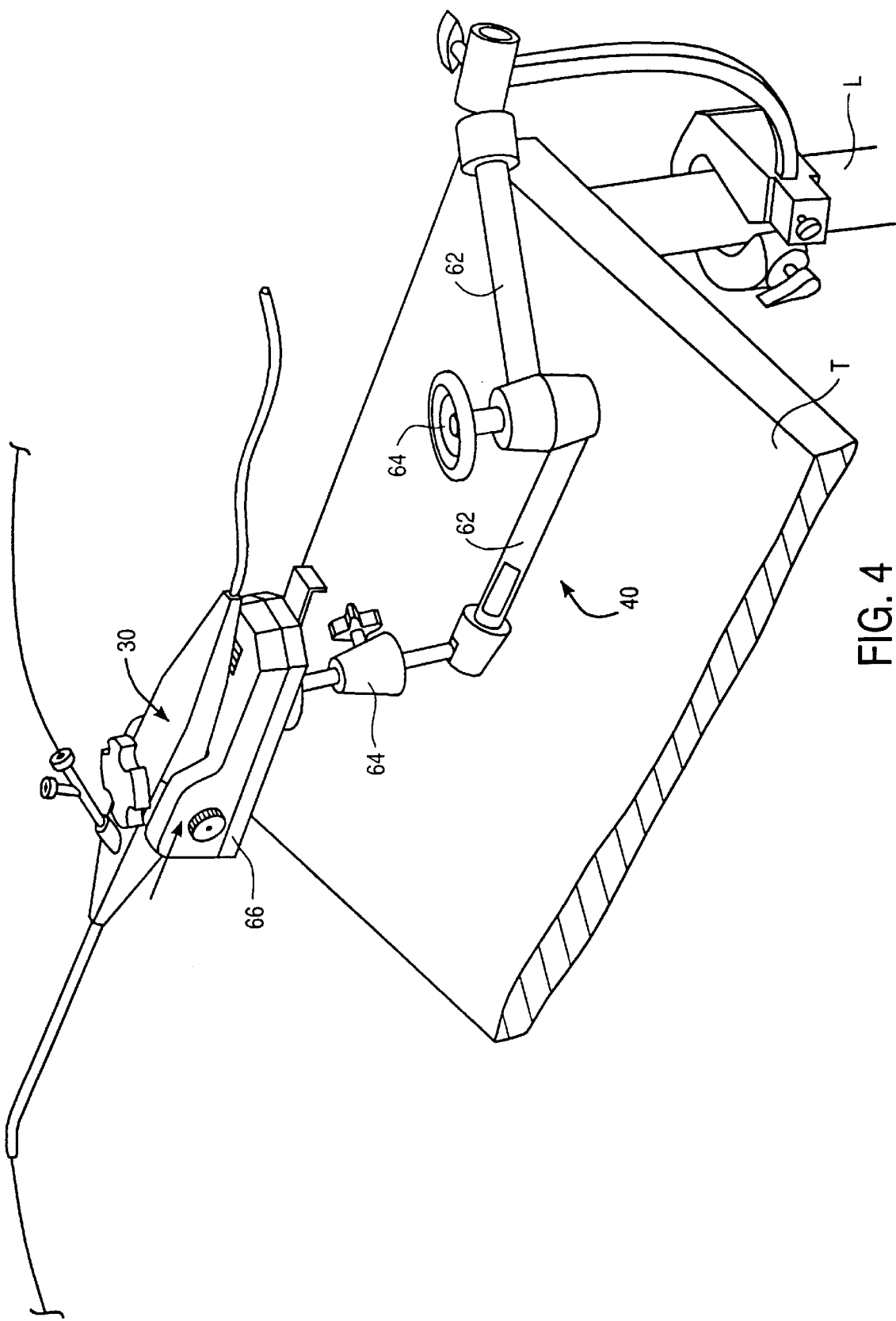
FIG. 4 illustrates a preferred method for supporting the proximal end of the hysteroscope according to the method of the present invention, wherein the proximal end is immobilized by a support structure attached to a table.

A particularly preferred method and apparatus for performing hysteroscopic and falloposcopic procedures, including retrograde imaging, is described in copending U.S. patent application Ser. No. 08/207,475, the full disclosure of which is herein incorporated by reference. As more fully explained in that application, a preferred method for performing falloposcopic procedures makes use of a hysteroscopic viewing scope 30 having a working shaft 32 with a deflectable distal end 34, as shown in FIGS. 3 and 4. Working shaft 32 is introduced to the uterus U, ideally using an adjustable support system 40. Deflectable distal end 34 is directed toward an ostium 36 of fallopian tube F. The uterus will be distended by introduction of irrigation fluid so that a guidewire may be directed into the fallopian tube using visualization through hysteroscope 30. Optionally, the guidewire 42 is disposed at the distal end of a catheter, as described hereinbelow. Alternatively, a conventional guidewire is first introduced to the fallopian tube, so that an access catheter 50 may be advanced over the guidewire in a conventional manner. Where such a conventional guidewire is used, it must generally be removed from a central lumen of positioned access catheter 50 to make room for falloposcope 14.

In order to further simplify the falloposcopic procedures of the present invention, support structure 40 immobilizes the viewing scope 30 on a table T or other surface, once the scope has been properly positioned in the uterus. Support structure 40 includes a plurality of arms 62 and joints 64 which are designed to freely articulate so that a support base 66 at a distal end of support structure 40 can be moved freely in space until locked into position. Preferably, the support structure is firmly secured to a table leg L. Such systems commercially available from suppliers such as Lino Manfrotto & Company.

Figure 5:
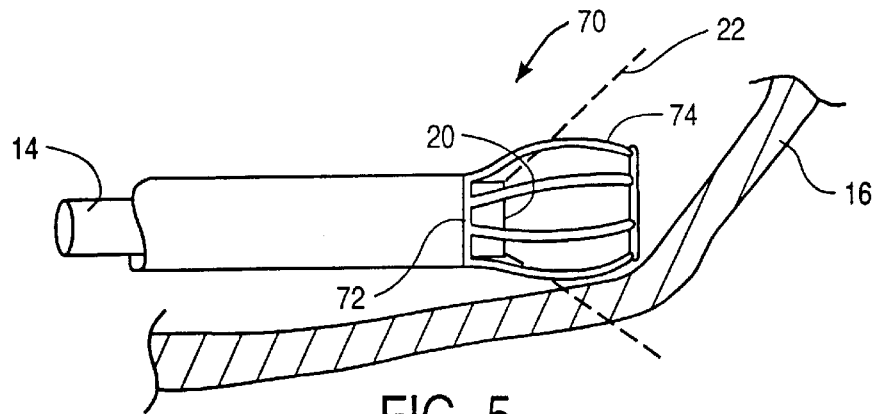
FIG. 5 illustrates a falloposcope which is separated from a tubal wall by an access catheter having a distal cage structure, according to the principles of the present invention.

Referring now to FIG. 5, a caged access catheter 70 slidably receives falloposcope 14 to a scope viewing position at which falloposcope distal end 20 is adjacent to a distal end of the catheter 72. A distal cage structure 74 surrounds distal scope end 20 to prevent the tubal wall of fallopian tube 16 from coming into such close proximity with the distal end of the scope that a white-out occurs.

Distal cage 74 separates the tubal wall from the scope viewing position by any of at least three different mechanisms. First, cage 74 prevents the tubal wall from collapsing immediately after catheter distal end 72 has passed, restraining the tubal wall in its distended position, thereby preventing encroachment of the tubal wall toward the scope. Second, distal cage 74 may reposition the entire distal portion of access catheter 70 away from the tubal wall to provide the necessary separation. Finally, distal cage 74 promotes axial alignment of catheter distal end 72 with the fallopian tube by providing an elongated distal moment arm through which the access catheter and tubal wall engage each other. This also promotes alignment between the falloposcope field of view 22 relative to the orientation of the local fallopian tube axis.

Figure 6:
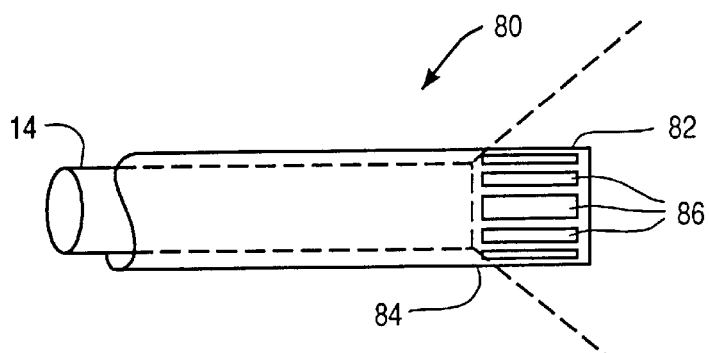
FIG. 6 illustrates an alternative cage structure formed by cutting axial viewing slots in a distal extension of the catheter body.

Referring now to FIG. 6, an alternative caged access catheter 80 is formed with a simplified cage 82. Simplified cage 82 comprises a continuation of the catheter body beyond catheter distal end 84, in which a plurality of viewing slots 86 have been cut. Both caged embodiments of the present access catheter generally provide substantially axisymmetric viewing through an open distal end of the caged structure and through viewing slots 86, or the analogous gaps between the cage structural elements. Rotation of such caged access catheters is generally not necessary to insure separation between the falloposcope and tubal wall, but will allow viewing of tubal wall elements which would otherwise be blocked during at least a portion of the scan.

Figure 7:
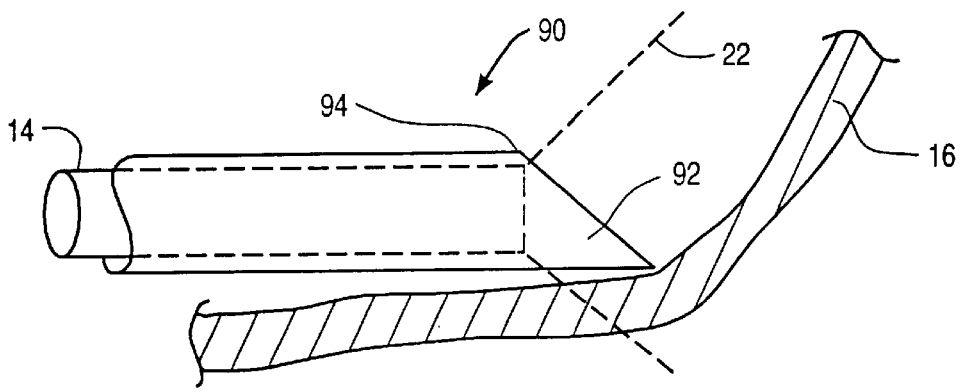
FIG. 7 illustrates a falloposcope which is separated from a fallopian tube wall by an access catheter having a distally protruding diagonal tip, in accordance with the principles of the present invention.
Figure 8:
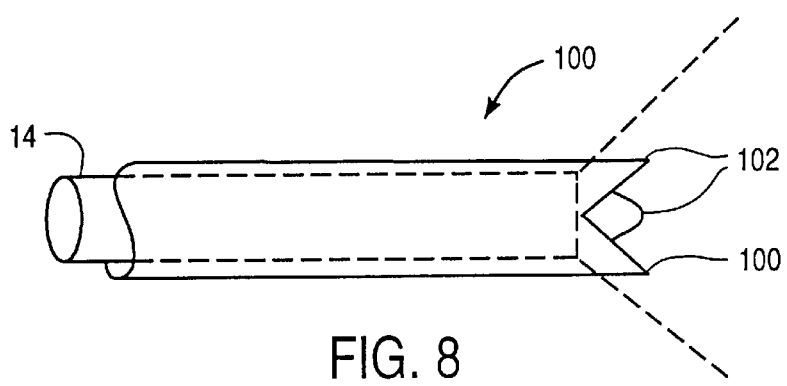
FIG. 8 illustrates an access catheter having a plurality of diagonal tips extending from the distal end of the catheter body, in accordance with the principles of the present invention.

Referring now to FIG. 7, a diagonal tip access catheter according to the present invention comprises a diagonal tip 92 extending distally from catheter distal end 94. It can be seen that diagonal catheter 90 must be rotated so as to engage tubal wall 16 with diagonal tip 92. It can also be seen that the field of view 22 is clear in much of the area where distal structure is not required to engage the tubal wall. The angle of diagonal tip 92 will typically be in the range between 45° and 80° from normal, and need not be constant nor extend the entire catheter width. A multiple angle access catheter 100 reduces the need for rotating the catheter, as seen in FIG. 8.

Figure 9A:
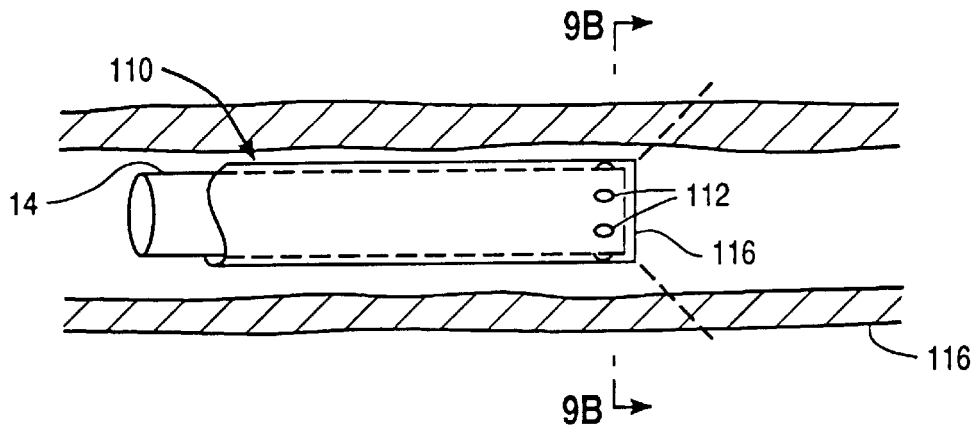
FIGS. 9A and B illustrate an access catheter having a plurality of side openings and a central lumen opening which provide a balanced flow path for irrigation fluid to maintain separation between the falloposcope and the tubal wall.
Figure 9B:
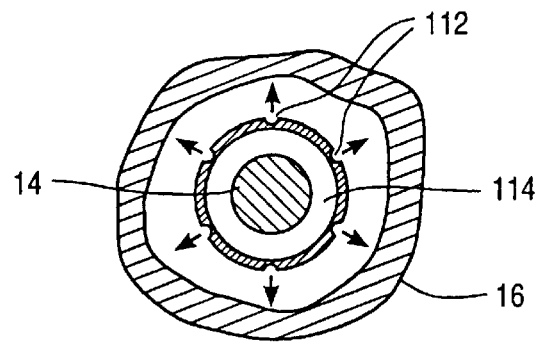

Referring now to FIGS. 9A and B, a fluid separating catheter 110 comprises a plurality of radial distal passages adjacent to the catheter distal tip 116. Radial passages 112 direct clear flush solution against the tubal wall of fallopian tube 16 to promote separation between falloposcope 14 and the tubal wall. Flush solution also flows out the distal tip 116 of fluid catheter 110 around falloposcope 14, thereby promoting separation between the distal end of the falloposcope and the tubal wall. The fluidic paths represented by the radial passages 112, are preferably balanced by varying the sizes of the radial passages relative to the open gap 114 between the catheter and falloposcope at the distal end.

A fixed distal guidewire access catheter 120 will be described with reference to FIGS. 10A through C. Guidewire catheter 120 comprises a distal guidewire 122 extending distally from a distal end of the catheter body 124, typically by a distance from 0.5 to 5 cm, ideally being 1 to 3 cm long and less than 0.02"in diameter. The catheter body includes a distal portion 126, typically being between 2.2 and 3.0 F, and first and second enlarged portions 128, 130. First and second enlarged portions 128, 130 reduce the pressure required for the introduction of clear flush around the falloposcope 14, as is more fully explained in copending U.S. patent application Ser. No. 08/207,475, the full disclosure of which has previously been incorporated by reference. A Touhy-Borst valve 132 is provided near the proximal end of the catheter to seal the proximal end and also allow access for falloposcope 14. An irrigation port 134 is also provided.

A particularly advantageous structure for supporting distal guidewire 122 comprises a distal ring coupler 125 which is fittingly inserted within distal portion 126 of guidewire catheter 120. The ring coupler provides effective support for the guidewire, but does not increase the proximal size or stiffness of the catheter body, and also maintains a smooth outer surface. Typically, the coupler ring and guidewire will comprise stainless steel, platinum, or a shape memory alloy such as Nitinol™, or the like. The guidewire will typically be coiled, but will ideally include an uncoiled portion extending to internal coupler ring 125, thereby minimizing the blockage of the catheter lumen.

Distal guidewire 122 is offset distally at an edge of guidewire catheter 120, and thereby allows the rotational engagement of the tubal wall described above regarding FIG. 7. Advantageously, the guidewire blocks the smallest possible imaging area, and also provides increased functionality for the catheter by allowing the catheter to be self-guided during introduction. Furthermore, the central lumen is not occupied by a conventional guidewire during advancement of the catheter into the fallopian tube, thereby providing the attending surgeon the option of advancing the falloposcope to the viewing position of guidewire catheter 120 to visually direct catheter advancement.

Figure 11A:
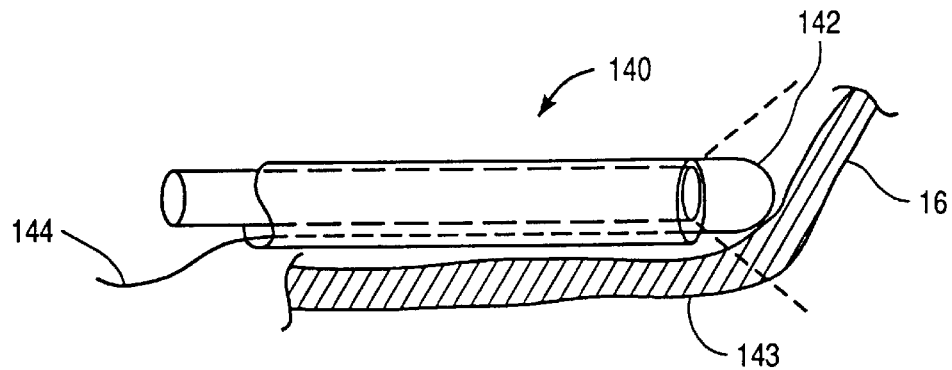
FIGS. 11A, B, C, and D illustrate access catheters having a guidewire which extends from the distal end of the catheter body to form a distal loop, which distal loop can be expanded by axially advancing a proximal extension of the guidewire, in accordance with the principles of the present invention.
Figure 11B:
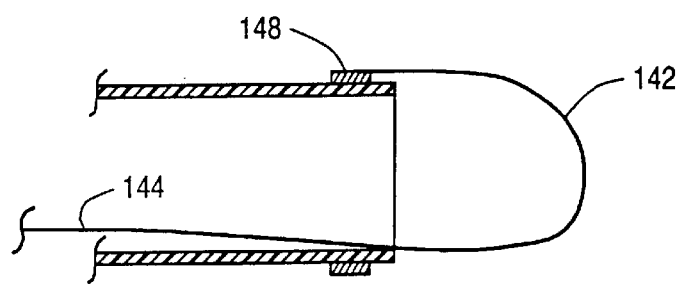
Figure 11C:
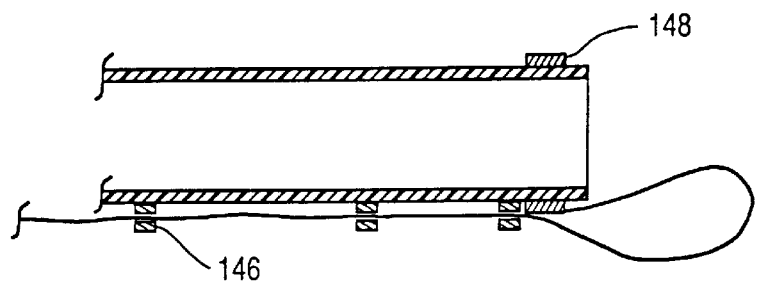
Figure 11D:
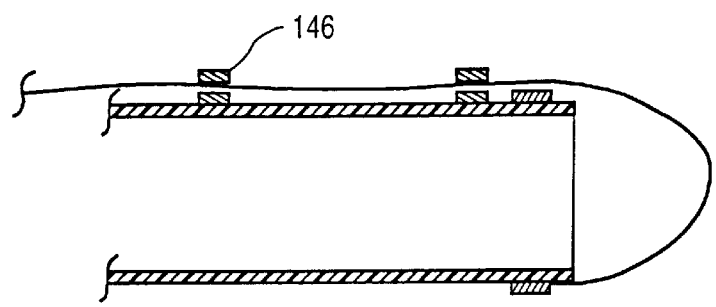

Referring now to FIGS. 11A through D, a looped guidewire access catheter 140 generally comprises a guidewire which extends distally from a distal catheter body end 143, the guidewire forming a distal loop 142. A proximal extension 144 of the guidewire runs along the length of the catheter body, allowing the distal loop to be manipulated by axially advancing and retracting extension 144 relative to the proximal end of the catheter body. As shown in FIGS. 11B through D, extension 144 may be disposed within the lumen of the catheter body, or may alternatively pass through guides 146 on the outer surface of the catheter. Alternatively, a separate lumen may be included in the catheter body, although this will require an increase in the cross-sectional size of the catheter. The guidewire may be attached to the distal end of the tip using coupler ring 125 (FIG. 10C), or may alternatively extend from a distal outer ring 148, or from the catheter lumen wall itself.

Advantageously, distal loop 142 provides an active mechanism for the surgeon to control the separation between the tubal wall and the falloposcope. By advancing extension 144 distally only when a white-out condition occurs, the distance between the tubal wall and the scope may be varied without having to move the scope itself. The guidewire loop may further be retracted when not in use, and may also be biased to assume a particular distal shape, as seen in FIG. 11C.

Figure 12A:
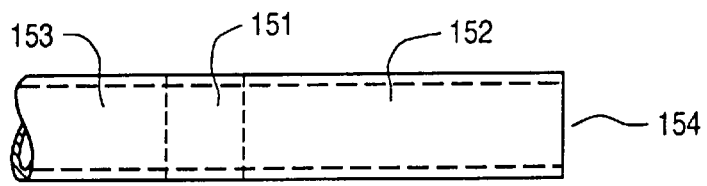
FIGS. 12A and B illustrate an access catheter having an extended diagonal tip formed by joining different tubes and cutting the joined tubes along a curve.
Figure 12B:
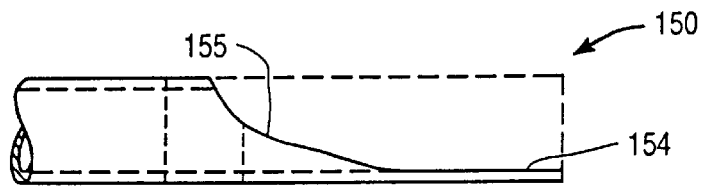

FIGS. 12A and B illustrate a particularly advantageous access catheter 150 which is formed by joining an intermediate tube 151 and an end tube 152 to catheter body tubing 153. The tubes may be adhesively bonded, or preferably melted together. The durometer of the tubing increases toward the distal end 154. A curved cut forms an extended diagonal tip 157. Proper selection of tubing materis, together with careful shaping of the extended tip 157, provides control over the flexibility of the distal structure. Clearly, the tip shape may comprise a smooth curve or a series of angles, and any number of tubing sections may be joined, within the scope of the present invention. Advantageously, extended diagonal tip 157 provides the functionality of a distal guidewire, but with an easily fabricated, uninterrupted structure.

Although the foregoing invention has been described in some detail by way of illustration and example, for purposes of clarity and understanding, it will be obvious that certain changes and modifications may be practiced within the scope of the appended claims.

What is claimed is:

1. A catheter for viewing a wall of a narrow body lumen, the catheter comprising:

an optical viewing scope including illumination fibers and viewing fibers within a single shaft;

a flexible elongate tubular body having a proximal end, a distal end, and a central lumen therebetween, the lumen slidably receiving the shaft of the optical viewing scope such that the optical scope extends distally to a viewing position adjacent to the distal end of the body; and a spacing structure, comprising a plurality of diagonal tips extending distally from the distal end of the body so as to maintain separation between the scope viewing position and the lumen wall.

2. A catheter as claimed in claim 1, wherein the catheter body includes a single axial lumen.

3. A catheter as claimed in claim 1, wherein the plurality of tips have angles between 45° and 80° from the normal to the lumen.

4. A catheter as claimed in claim 3, wherein the diagonal tip angle of the plurality of tips extend along the length of the tip.

5. A catheter as claimed in claim 3, wherein the diagonal tip angles of the plurality of tips are not constant along the diagonal tips.

6. A catheter for viewing a wall of a narrow body lumen in combination with an optical viewing scope of the type including illumination fibers and viewing fibers within a single shaft, the catheter comprising:

a flexible elongate tubular body having a proximal end, a distal end, and a central lumen therebetween, the lumen slidably receiving the shaft of the optical viewing scope to a scope viewing position adjacent to the distal end of the body; and a spacing structure extending distally from the distal end of the body so as to slidably contact the lumen wall and maintain separation between the scope viewing position and the lumen wall, wherein the spacing structure comprises a diagonal tip extending from the distal end of the body, wherein the diagonal tip comprises a stiff material relative to the material used to form the elongate tubular body, and an intermediate material disposed between the stiff material and the elongated tubular body and wherein the diagonal tip is defined by a curve or angle.

7. A catheter as claimed in claim 6, wherein the diagonal tip comprises a plurality of intermediate materials.

8. A catheter as claimed in claim 6, wherein the diagonal tip has an axial flexibility and length suitable for the diagonal tip to provide the functionality of a distal guidewire.

9. A catheter as claimed in claim 6, wherein durometers of the materials increase toward the distal end.

* * * * *